(12) United States Patent
Holland

(10) Patent No.: US 7,435,878 B2
(45) Date of Patent: Oct. 14, 2008

(54) METHOD FOR ALTERING THE MALE FERTILITY OF PLANTS

(75) Inventor: Mark A. Holland, Salisbury, MD (US)

(73) Assignee: Salisbury University, Salisbury, MD (US)

( * ) Notice: Subject to any disclaimer, the term of this patent is extended or adjusted under 35 U.S.C. 154(b) by 553 days.

(21) Appl. No.: 10/296,158

(22) PCT Filed: May 22, 2001

(86) PCT No.: PCT/US01/16321

§ 371 (c)(1), (2), (4) Date: Nov. 22, 2001

(87) PCT Pub. No.: WO01/90303

PCT Pub. Date: Nov. 29, 2001

(65) Prior Publication Data

US 2003/0211082 A1    Nov. 13, 2003

Related U.S. Application Data

(60) Provisional application No. 60/206,376, filed on May 23, 2000.

(51) Int. Cl.
*A01G 7/00* (2006.01)
*A01N 63/00* (2006.01)
*A01C 1/06* (2006.01)

(52) U.S. Cl. .................. 800/303; 800/260; 800/298; 800/320.2; 800/306; 435/243; 504/100; 504/117; 71/6

(58) Field of Classification Search ................ 504/100; 800/298, 320.2, 306, 312, 303
See application file for complete search history.

(56) References Cited

U.S. PATENT DOCUMENTS

| | | | |
|---|---|---|---|
| 5,106,648 A | 4/1992 | Williams | |
| 5,268,171 A | 12/1993 | Polacco et al. | |
| 5,415,672 A | 5/1995 | Fahey et al. | |
| 5,512,069 A | 4/1996 | Holland et al. | |
| 6,329,320 B1 | 12/2001 | Joshi et al. | |

OTHER PUBLICATIONS

Hannu Ahokas. PNAS (1982), vol. 79, pp. 7605-7608.*

* cited by examiner

*Primary Examiner*—Medina A. Ibrahim
(74) *Attorney, Agent, or Firm*—William E. Beaumont

(57) ABSTRACT

A method for altering fertility of a plant or modifying its structure is described. The method comprises, in any order, contacting the seed of the plant with Pink-Pigmented Facultative Methylotroph (PPFM) that in the aggregate produces more or less amount of cytokinin than the PPFM that was previously associated with the plant, and then planting the seed.

18 Claims, 5 Drawing Sheets

METHOD FOR ALTERING THE MALE FERTILITY OF PLANTS

This application claims the benefit of priority date of U.S. Provisional Application No. 60/206,376, filed May 23, 2000, the content of which is incorporated into the present application in its entirety.

BACKGROUND OF THE INVENTION

1. Field of the Invention

The present invention relates to the field of plant biotechnology. The present invention also relates to control of plant morphology and fertility with plant symbiotic bacteria that produce varying amounts of cytokinin.

2. Brief Description of the Related Art

Previously, it has been demonstrated that Pink-Pigmented Facultative Methylotroph (PPFM) bacteria, especially *Methylobacterium spp.*:

- are distributed ubiquitously on plants (Corpe, W. A. & Basile, D. V. (1982) *Dev. Indust. Microbiol.* 23, 483-493; and Corpe, W. A. & Rheem, S. (1989) *FEMS Microbiol. Ecol.* 62, 243-250),
- are present in large numbers (Hirano, S. S. & Upper, C. D. (1992) in *Microbial Ecology of Leaves*, eds. Andrews, J. H. & Upper, S. S. (Springer, New York), pp. 271-279),
- stimulate plant growth in vitro (Basile, D. V., Slade, L. L., & Corpe, W. A. (1969) *Bull. Torrey Bot. Club* 96(6), 711-714; and Basile, D. V., Basile, M. R., Li, Q. Y., & Corpe, W. A. (1985) *Bryologist* 88(2), 77-81),
- participate in plant nitrogen metabolism (Holland, M. A & Polacco, J. C. (1992) *Plant Physiol.* 98, 942-948; Stebbins, N. E., Holland, M. A., Cianzio, S. R., & Polacco, J. C. (1991) *Plant Physiol.* 97, 1004-1010)
- enhance seed germination (Holland, M. A. & Polacco, J. C. (1994) *Annu. Rev. Plant Physiol. Plant Mol. Biol.* 45, 197-209)
- stimulate root growth (Holland, M. A. (1997) *Recent Res. Devel. in Plant Physiol.* 1, 207-213)

Most recently, we have demonstrated in soybean that foliar applications of the bacteria to plants under adverse field conditions can produce a 70% increase in seed yield over untreated plants, as described in U.S. Pat. No. 5,961,687, which is incorporated by reference herein in its entirety. The seemingly varied effects of this bacterium on plant performance are explained by its production of the plant growth regulator, cytokinin (Freyermuth, S. K., Long, R. L. G., Mathur, S., Holland, M. A., Holtsford, T. P., Stebbins, N. E., Morris, R. O., & Polacco, J. C. (1996) in *Microbial Growth on C1 Compounds*, eds. Lidstrom, M. E. & Tabita, F. R. (Kluwer, Dordrecht), pp.277-284). So, it is reasonable to consider other physiological effects of cytokinins on plants and to investigate whether PPFMs can also be used to alter them. One such physiological effect is on normal flower development and fertility.

*Methylobacterium* is a seed-transmitted bacterium. That is, the bacteria are incorporated into developing seeds and are reliably passed from generation to generation. Because of the way the bacteria are inherited, any trait they confer on their host plant will look like an example of "maternal" or "cytoplasmic" inheritance. A classic example of this pattern of inheritance is given by cytoplasmic male sterility, a trait which is exploited for the production of F1 hybrid seed. Several different and independently-operating mechanisms are known to account for cytoplasmic male sterility. Plant growth regulators, including cytokinin, are known to influence sex expression in many plant species (Frankel, R. & Galun, E. (1977) *Pollination mechanisms, reproduction and plant breeding*, Springer Verlag, Berlin. 218 pp).

*Methylobacterium* produces cytokinin and it passes from generation to generation in the same pattern as cytoplasmic genes. Interestingly, it has been shown in barley that cytoplasmic male sterile plants (CMS) are characterized by abnormally low levels of cytokinins (Ahokas (1982) *Proc. Nat. Acad. Sci. USA.* 79:7605-7608). If bacteria are an important natural source of cytokinins in plants (Holland, M. A. (1997) *Plant Physiol* 115, 865-968), then differences between bacterial strains with respect to cytokinin production could be responsible for a host of differences in growth and development between plant varieties—including fertility. Thus, different strains of *Methylobacterium* can be used to produce and correct male sterility in a variety of plants.

SUMMARY OF THE INVENTION

The present invention is among other things, directed to a method for altering the fertility of plants, the production of F1 hybrid seed and development of novel ornamental plant varieties.

In one aspect of the invention, the invention is directed to a method for increasing fertility of a plant, comprising, in any order:

(a) contacting seed of the plant with Pink-Pigmented Facultative Methylotroph (PPFM) that in the aggregate produces a greater amount of cytokinin than the PPFM that was previously associated with the plant; and (b) planting the seed.

In this method, the increasing fertility is indicated by increasing pollen count. The plant is a dicot or a monocot. Most preferably, the plant is soybean, barley, *Arabidopsis*, or *Celosia*. Moreover, the cytokinin is trans-Zeatin and/or its riboside.

The method described above may further include treating the seed to remove the previously associated PPFM before contacting the seed with the PPFM that produces greater amount of cytokinin than the previously associated PPFM.

Alternatively, the method described above may further comprise contacting the seed with more of the previously associated PPFM to produce more cytokinin in the aggregate.

In another aspect of the invention, the invention is directed to a method for decreasing fertility of a plant, comprising, in any order:

(a) contacting seed of the plant with Pink-Pigmented Facultative Methylotroph (PPFM) that in the aggregate produces lesser amount of cytokinin than the PPFM that was previously associated with the plant; and (b) planting the seed.

In this method, the decreasing fertility is indicated by decreasing pollen count. The plant is a dicot or a monocot. Most preferably, the plant is soybean, barley, *Arabidopsis*, or *Celosia*. Moreover, the cytokinin is trans-Zeatin and/or its riboside.

The method described above may further include treating the seed to remove the previously associated PPFM before contacting the seed with the PPFM that produces lesser amount of cytokinin than the previously associated PPFM.

Alternatively, the method described above may further comprise contacting the seed with less of the previously associated PPFM to produce less cytokinin in the aggregate.

In still another aspect of the invention, the invention is directed to a method for obtaining F1 hybrid seeds of a plant comprising:

(a) contacting seed of the plant with Pink-Pigmented Facultative Methylotroph (PPFM) that in the aggregate produces low amounts of cytokinin;
(b) planting the seed and allowing the plant to grow;
(c) pollinating a flower from the plant with pollen from a source of interest; and (d) obtaining the F1 hybrid seeds.

This method may further comprise contacting the F1 hybrid seeds with wild-type or high level cytokinin expressing PPFM to obtain a fertile plant.

In yet another aspect of the invention, the morphology of a plant is altered by the use of the PPFM. The invention provides a method for making a new ornamental plant variety from previously identified ornamental plant, comprising:
(a) treating seeds of the identified ornamental plant to remove previously associated PPFM;
(b) contacting the treated seed with PPFM that either over- or under-produce cytokinin;
(c) planting the treated seeds and allowing the plant to grow; and
(d) selecting for an ornamental phenotype of interest.

An example of an ornamental plant is *Celosia*.

In another embodiment of the invention, the invention is directed to a method for increasing fertility of a plant, comprising:
(a) contacting the plant with PPFM that in the aggregate produces greater amount of cytokinin than the PPFM that was previously associated with the plant; and
(b) testing for its fertility.

In this method, the PPFM may contact the plant on its seed, its shoot or its root.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given hereinbelow, and the accompanying drawings which are given by way of illustration only, and thus are not limitative of the present invention, and wherein.

DETAILED DESCRIPTION OF THE INVENTION

Figure 1:
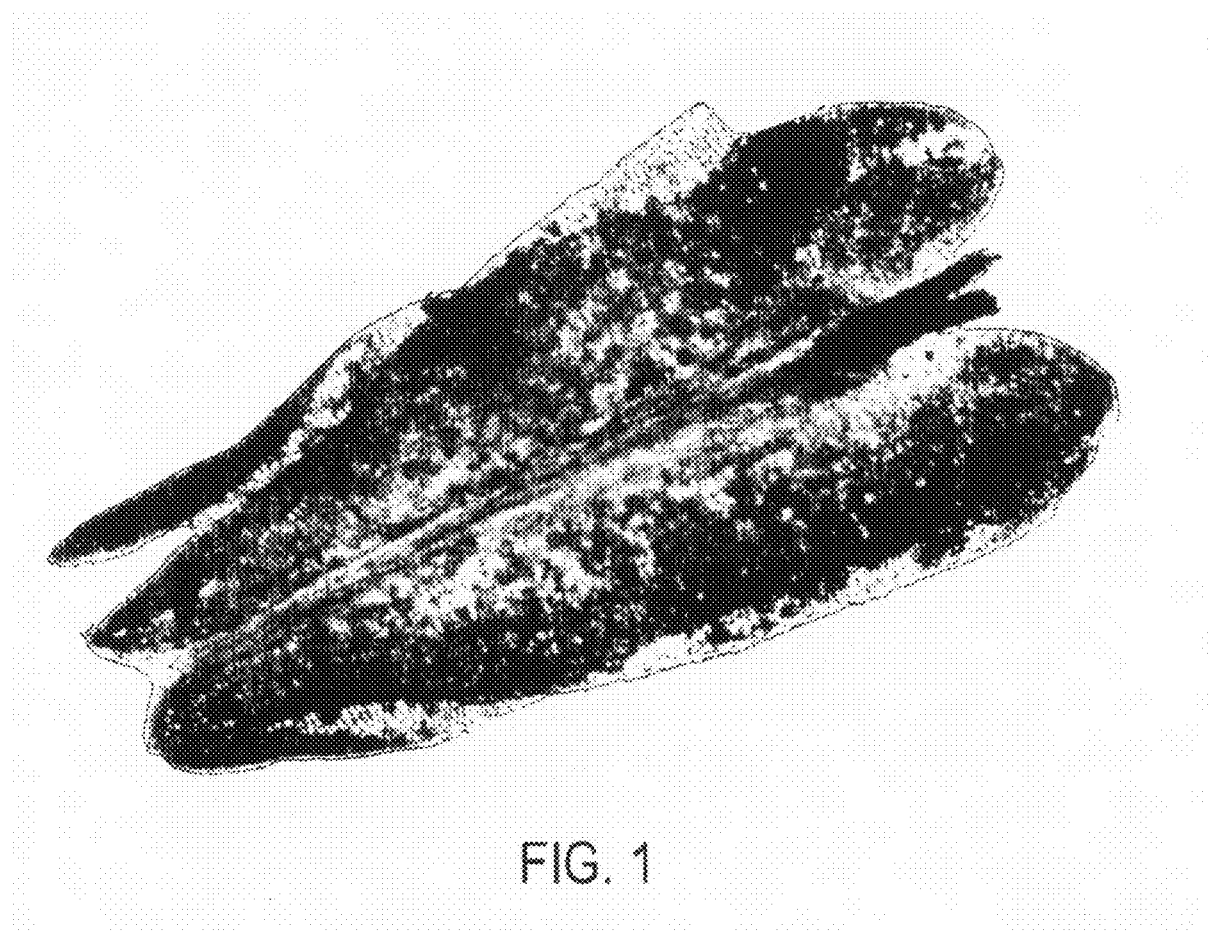
FIG. 1 shows a light microscope picture at 40× magnification, of anthers dissected from the flowers of cytoplasmic male sterile barley plants grown from seeds that were soaked in a suspension of wild type PPFM cells. Note that the anther is filled with pollen grains.

As used herein, "cytokinin" refers to a class of compounds structurally related to adenine, but substituted at the N6 position of the purine ring. These compounds promote cell division in plants. The most common form of naturally occurring cytokinin in plants is trans-zeatin which was isolated from corn (*Zea mays*). Cytokinins have been shown to promote cell enlargement of excised cotyledons from radish, pumpkin, cocklebur, flax, and other dicotyledonous plants. Cytokinins have been found in almost all higher plants as well as mosses, fungi, bacteria, and also in tRNA of many prokaryotes and eukaryotes. Today there are more than 200 natural and synthetic cytokinins combined. Examples of free cytokinins are zeatin and isopentenyladenine. There are also conjugated forms of cytokinins which can be produced in a number of ways. Glucosides can be formed by the attachment of carbon 1 of glucose to the hydroxyl group on the side chain of zeatin or the carbon 1 can attach to the. N atom of the C—N bond at either position 7 or 9 on the adenine ring. Another alternative is to form an alanine conjugate at position 9. The glucoside conjugates may represent storage forms or in some cases facilitate transport of certain cytokinins, whereas alanine conjugates are more likely to be irreversibly formed products which can serve as a detoxification mechanism in the plant. Degradation of cytokinins occurs largely by cytokinin oxidase. This enzyme removes the five carbon side chain and releases free adenine from zeatin and free adenosine from zeatin riboside.

As used herein, "cytoplasmic male sterile plant (CMS)" refers to that plant which fails to produce viable pollen and which failure is inherited maternally.

As used herein, "fertility" means the ability to produce viable gametes, preferably pollen.

As used herein, "normally associated PPFM" means PPFM bacteria of a type usually found on a plant.

As used herein, "previously associated PPFM" means PPFM bacteria of the type found on a plant prior to experimental manipulation.

As used herein, "substantially no cytokinin" refers to amounts of cytokinin at or below the limits of detection of the ELISA assay used here for quantification.

As used herein, "low amounts of cytokinin" refers to amounts less than 50% of that produced by other plants of the same species.

As used herein, "over-producing cytokinin" refers to strains of PPFM bacteria that secrete greater amounts cytokinin into their culture medium than do other PPFM isolates from the same plant species.

As used herein, "under-producing cytokinin" refers to strains of PPFM bacteria that secrete lesser amounts cytokinin into their culture medium than do other PPFM isolates from the same plant species It is understood that with regard to the measurement of the amount of cytokinin released to the plant, the numbers will be different for every experiment depending on how old the cultures (or plant tissue) are and also depending on the assay method used. It is understood that what matters is the relative amount measured in different cultures or tissues in the same experiment that affects a certain phenotype, such as the change in fertility or morphology of the plant.

As used herein, "PPFM" is an abbreviation for Pink-Pigmented Facultative Methylotroph. Preferably, PPFM includes, but is not limited to, *Methylobacterium mesophilicum, Methylobacterium organophilum, Methylobacterium extorquens, Methylobacterium fujisawaense, Methylobacterium radiotolerans, Methylobacterium rhodesianum, Methy-*

*lobacterium rhodinum*, or *Methylobacterium zatmanii*. In the most preferred embodiment, the microorganism is *Methylobacterium mesophilicum*.

The type of plants that can be altered by the method of the invention include, but not limited to, nonvascular plants, vascular plants, gymnosperms, angiosperms, dicots, or monocots. Preferably, the plant belongs to the vascular plants. More preferably, the plant is an angiosperm. More preferably, the plant is soybean, barley, *Arabidopsis*, and flowering plants such as *Celosia*. Particularly useful plants include plant and ferns of the genera: *Populus, Ermophilia, Lycopersicon, Nicotiana, Cannabis, Pharbitis, Apteria, Psychotria, Mercurialis, Chrysanthemum, Polypodium, Pelargonium, Polytrichiales, Mimulus, Chamomile, Monarda, Solanum, Achillea, Valeriana, Ocimum, Medicago, Aesculus, Newcastelia, Plumbago, Pityrogramma, Phacelia, Avicennia, Tamarix, Frankenia, Limonium, Foeniculum, Thymus, Salvia, Kadsura, Beyeria, Humulus, Mentha, Artemisia, Nepta, Geraea, Pogogstemon, Majorana, Cleome, Cnicus, Parthenium, Ricinocarpos, Parthenium, Hymenaea, Larrea, Primula, Phacelia, Dryopteris, Plectranthus, Cypripedium, Petunia, Datura, Mucuna, Ricinus, Hypericum, Myoporum, Acacia, Diplopeltis, Dodonaea, Halgania, Cyanostegia, Prostanthera, Anthocercis, Olearia, Viscaria*.

In the seed treatment method of the invention, the treatment method can be any method so long as the microorganism is able to bind to the seed. Such a method may include taking dry plant seeds and soaking them in suspensions of washed cells of the mutants, preferably for about 6 hours, and allowing the seeds to imbibe the mutant bacteria. Following this treatment, the seeds can be planted as normal to produce treated plants. Control seeds also can be planted to produce control plants. Harvested tissue from the treated plants is assayed for increased or decreased amounts of cytokinin as compared with control plants. Another treatment method may utilize electricity to cause the microorganism to adhere to the plant seed. Another method may use the PPFMs as a seed coating or powdered inoculum.

The PPFM used in the instant invention may be wild-type or a mutant. The mutant may be a natural mutant, or it may be created by genetic engineering methods. The introduction and transfer of non-genetically altered or genetically engineered strains can be accomplished by several methods. For example, treated or untreated seed can be imbibed in bacterial suspensions. Bacterial-associated embryos can be propagated under cell culture isolation that induces plantlet formation. Plant tissue cultures can be co-cultivated with, or inoculated with the bacteria. Another method capable of introducing and transferring the bacterium to the host plant is to vacuum infiltrate bacteria into seedlings or somatic embryos. Plant cuttings can be rooted in water or nutrient solutions containing bacteria. Finally, plants can be sprayed with a suspension of bacterial cells.

As used herein, "non-genetically engineered" PPFM mutant means any mutant that is isolated from a natural sample, and thus called "naturally occurring". Alternatively, the bacteria may be exposed to a mutagenizing amount of chemicals, radiation, or stress and mutants with altered phenotypes can be isolated. The phenotype of the mutants may be, but is not limited to, altered expression of a cytokinin.

Various prior art methods of genetically altering bacteria can be used in accordance with the present invention. For example, spontaneous and induced mutants can be recovered and selected for resistance to a series of antibiotics, such as pipericillin, rifampicin, etc. If desired, multiple resistances can be assembled.

An alternate approach for obtaining the bacteria is to recover bacteria that have acquired promiscuous plasmids bearing drug resistance (gene conferring drug inactivation) by non-genetically engineered methods.

Another method of altering the bacteria is to recover bacteria resistant to, or able to inactivate herbicides such as glyphosate and sulfonyl urea which inhibit the 5-enolpyruvylshikimic acid-3-phosphate synthase and acetolactate dehydrogenase, respectively.

Once bacterial strains are selected, seeds of plants can be soaked in suspensions containing these strains and allowed to imbibe bacterial cells. Such treated seeds can be planted. Mature plant and seed products can be harvested and tested for an increase or decrease in cytokinin, and differences in the fertility and morphology of the plant.

Although seeds may be directly contacted with PPFM, it is understood that PPFM may be applied on to plant foliage, on to plant seeds, or on to the soil in which plants will be propagated.

In the production of male sterile lines for breeding purposes, the following set of steps may be followed.

A. Select seeds to be made "male sterile". For the purposes of producing F1 hybrid seed, plants grown from this seed will be used as the female parent. It is noted that this could be any plant.

B. Treat seeds of the female parent to remove native PPFMs. This is may be carried out by for example, heating the dry seeds in a dry oven at 50° C. for 48 hours, but other methods, like the use of antibiotics are also feasible.

C. Inoculate the treated seeds in a suspension of low-cytokinin-producing PPFMs like those isolated from cytoplasmic male sterile barley. Usually, this is done by imbibing the dry seeds in a liquid suspension of the bacteria, but see also methods described in U.S. Pat. No. 5,512,069, which is incorporated by reference herein in its entirety.

D. Plant seeds. Flowers are expected to be male sterile.

E. Pollinate with pollen from desired male parent. Collect hybrid seed.

F. Inoculate hybrid seeds with normal PPFMs to restore fertility in the F1 generation.

In another embodiment of the invention, the method of the invention may be used to restore fertility to previously identified cytoplasmic male sterile plants by using the following exemplified steps:

A. Obtain plant seeds of cytoplasmic male sterile.

B. Pollinate with pollen from a desired male parent. Collect hybrid seed.

C. Inoculate hybrid seeds with normal PPFMs to restore fertility in the F1 generation.

In yet another embodiment of the invention, the method of the invention may be used to create a new and unique ornamental plant variety from a previously identified ornamental plant.

A. Treat seeds of the ornamental variety to remove native PPFMs as described above.

B. Inoculate the treated seeds with PPFMs that either over- or under-produce cytokinins.

C. Plant the treated seeds and make selections for unusual ornamental phenotypes. Expected phenotypes include double flowers, fasciated stems, increased branching and flowers of unusual size, for example.

The following examples are offered by way of illustration of the present invention, and not by way of limitation.

EXAMPLES

Example 1

Cytokinin under-producing strains of *Methylobacterium* colonize the cytoplasmic male sterile barley and the low levels of cytokinin found in the plant are the reason for reduced fertility. To test this, *Methylobacterium* from both cytoplasmic male sterile and normal barley plants was isolated. Cytoplasmic male sterile barley was obtained from the National Plant Germplasm System—Small Grains Collection, at Aberdeen, Idaho. Wild type barley was obtained from a local seed merchant. PPFM isolates were obtained as previously described in Holland, M. A & Polacco, J. C. (1992) *Plant Physiol.* 98, 942-948, which is incorporated by reference herein in its entirety. Liquid cultures of the isolates were grown and 0.1 mL aliquots of the spent medium were assayed by Enzyme Linked Immunosorbent Assay (ELISA) for trans-Zeatin riboside content using a commercially available ELISA kit (Sigma Chemical Co., St. Louis, Mo.). In repeated experiments, the culture supernatant of PPFMs isolated from cytoplasmic male sterile barley contained only 10% as much trans-Zeatin riboside as that of the isolate from wild type barley (0.016 vs. 0.19 pmol/0.1 mL and 0.013 vs. 0.14 pmol/ 0.1 mL in two different experiments, for example).

Example 2

If low cytokinin levels in plants can cause male sterility, then applying cytokinin over-producing bacteria to the male steriles should restore fertility. This is very important since it is the ability to restore fertility to male sterile plants that determines whether they can be used for producing F1 hybrid seed. To test whether fertility could be restored to cytoplasmic male sterile barley plants by introducing PPFM bacteria isolated from wild type barley plants, cytoplasmic male sterile barley seeds were soaked in a suspension of wild type PPFM cells for 6 hours before planting as described in, for example, U.S. Pat. No. 5,512,069, which is incorporated herein by reference in its entirety.

Figure 2:
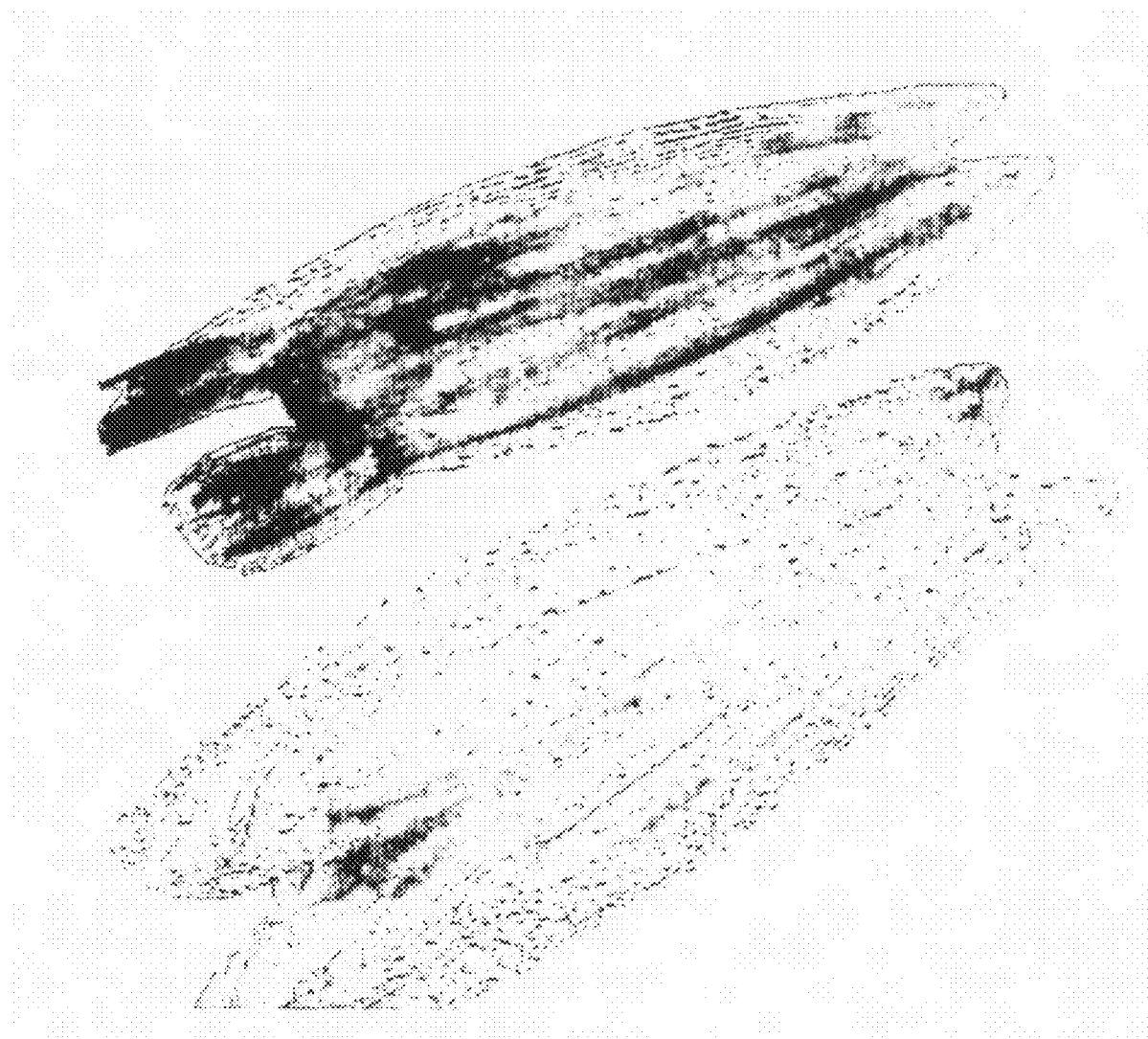
FIG. 2 shows a light microscope picture at 40× magnification, of anthers dissected from the flowers of cytoplasmic male sterile barley plants grown from control seeds that were not treated with PPFM cells. Note that the anther is devoid of pollen grains.

For this experiment, no further application of PPFMs was made. At flowering, low (but persistent) levels of seed set were observed on the treated plants. No seeds were produced on untreated controls. Anthers dissected from the flowers of treated plants contained pollen, while the anthers of untreated plants were shriveled and empty. See FIGS. 1 and 2.

Example 3

Cytokinin production (ng of trans-Zeatin riboside/liter of culture) by bacterial isolates from a) wild type barley, b) cytoplasmic male sterile barley (CMS), and c) CMS barley plants inoculated before planting with bacteria from the wild type plant (CMS+wild). Three separate determinations were made for a) and b) representing three separate experiments. Note that cytokinin production is routinely 10-fold higher in bacteria from wild type plants than in bacteria from CMS plants. Also, bacteria from CMS plants inoculated with bacteria from wild type plants (and these are the plants that show restoration of fertility) produce cytokinins at wild type levels. The results are shown in Table 1 below.

TABLE 1 trans-Zeatin riboside produced by barley isolates (ng/L)

| | | Experiment 1 | Experiment 2 | Experiment 3 |
|---|---|---|---|---|
| a | Wild type | 668 | 492 | 1160 |
| b | CMS | 56 | 46 | 91 |
| c | CMS + Wild type | not determined | not determined | 808 |

Example 4

Replacement of a plant's normal bacterial population with cytokinin under-producers might be expected to produce male sterility. If indeed this is the case, then male sterility could be induced at will in any breeding line. Such a finding would be of enormous significance and utility to plant breeders. Another treatment that could mimic inoculation with low cytokinin producing lines could be simply to lower the number of normal cytokinin producers. This experiment is conducted on wild-type barley, *Arabidopsis* and soybean (*Glycine max*). Tissue has been harvested from some of the soybean plants in this study and assayed for trans-Zeatin riboside as described above. As shown in Table 2 below, tissue which received heat treatments (i.e., with low levels of PPFMs) showed a reduced concentration of trans-Zeatin riboside. Heat treatment consists of 48 hours in a dry oven at 50° C. This treatment was shown earlier to reduce PPFM populations on seed, as described in for example, Holland, M. A & Polacco, J. C. (1992) *Plant Physiol.* 98, 942-948, which is incorporated herein by reference in its entirety. Reinoculation of heat-treated seed with wild type PPFM restored near-normal cytokinin levels. Observations of pollen development in treated plants indicates some abnormalities like germination of the pollen grains before anthesis.

TABLE 2 trans-Zeatin Riboside concentration in tissue extracts of soybean as a function of the amount of PPFM resident on them.

| Treatment | trans-Zeatin riboside (pmnol/0.1 mL extract) |
|---|---|
| No heat, No added PPFMs | 0.181 |
| No heat, PPFMs added | 0.219 |
| 48 hours heat, No PPFMs added | 0.113 |
| 48 hours heat, PPFMs added | 0.172 |

Example 5

Figure 5:
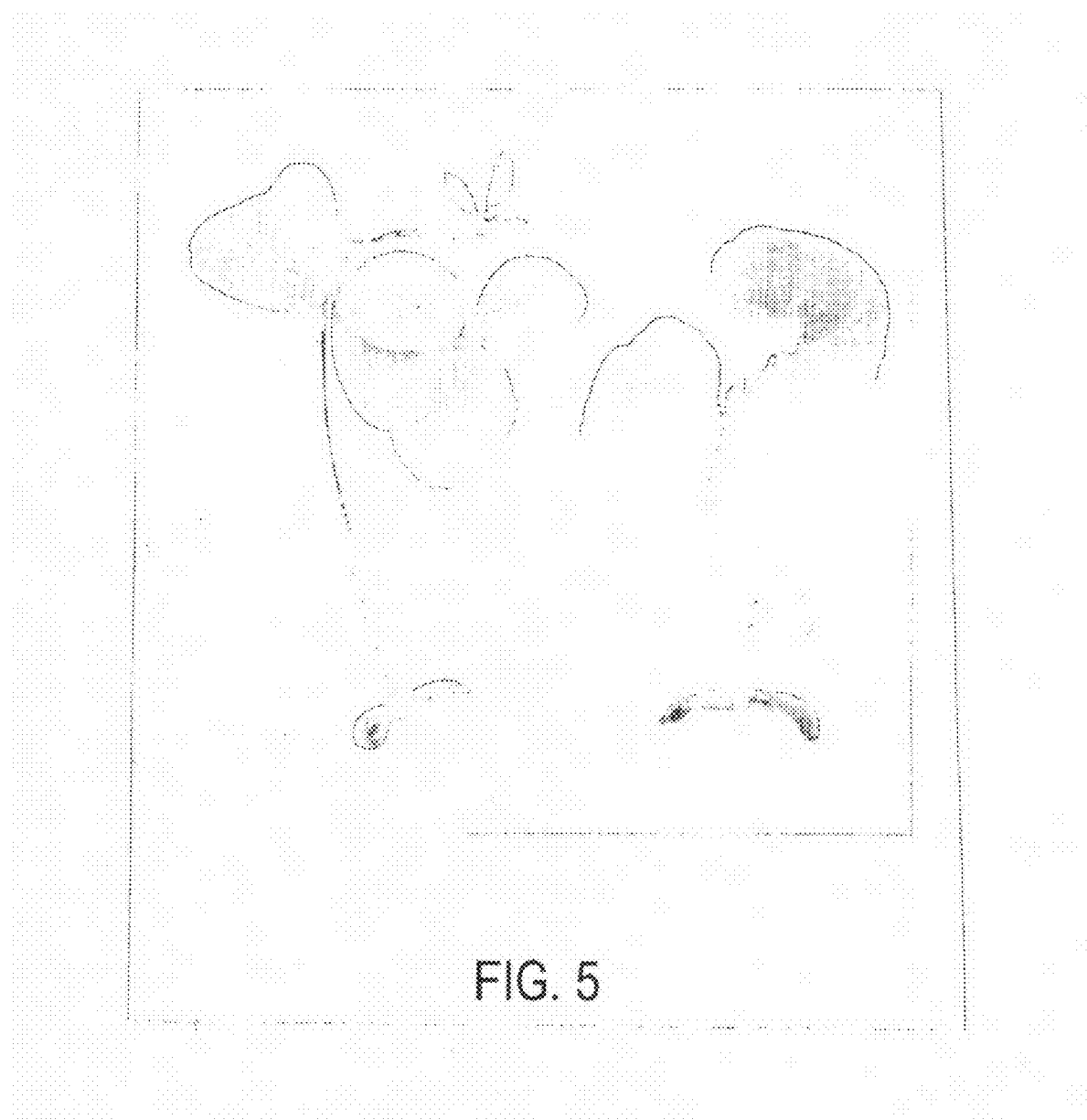
FIG. 5 shows soybean seedling grown from untreated seed (left), and seed treated with PPFM producing high amounts of cytokinin. Note that the treated seedling is branching.

Soybean seedlings are shown in FIG. 5. The plant on the left is normal (untreated). The plant on the right grew from a seed that was inoculated before planting with a PPFM bacterium that produces high levels of cytokinin. Note that the lateral buds on the plant on the right are developing to produce branching. This effect is associated with high levels of cytokinin. The experiment has been repeated on five different plants, always with the same result.

Example 6

Experiments Altering Flower Morphology

Figure 3:
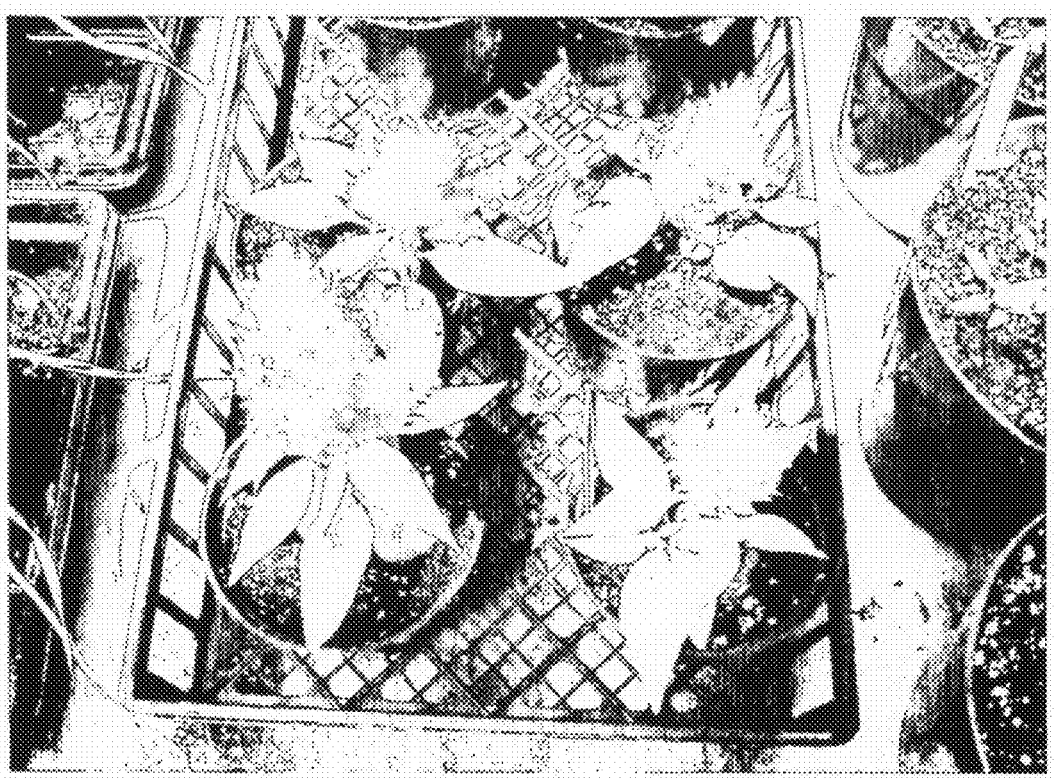
FIG. 3 shows *Celosia* 'plumosa'. The plumosa form of *Celosia* carries an open, plume-like inflorescence. PPFM bacteria isolated from these plants produce ten fold less cytokinin in culture than do PPFMs isolated from the 'cristata' form of the plant.
Figure 4:
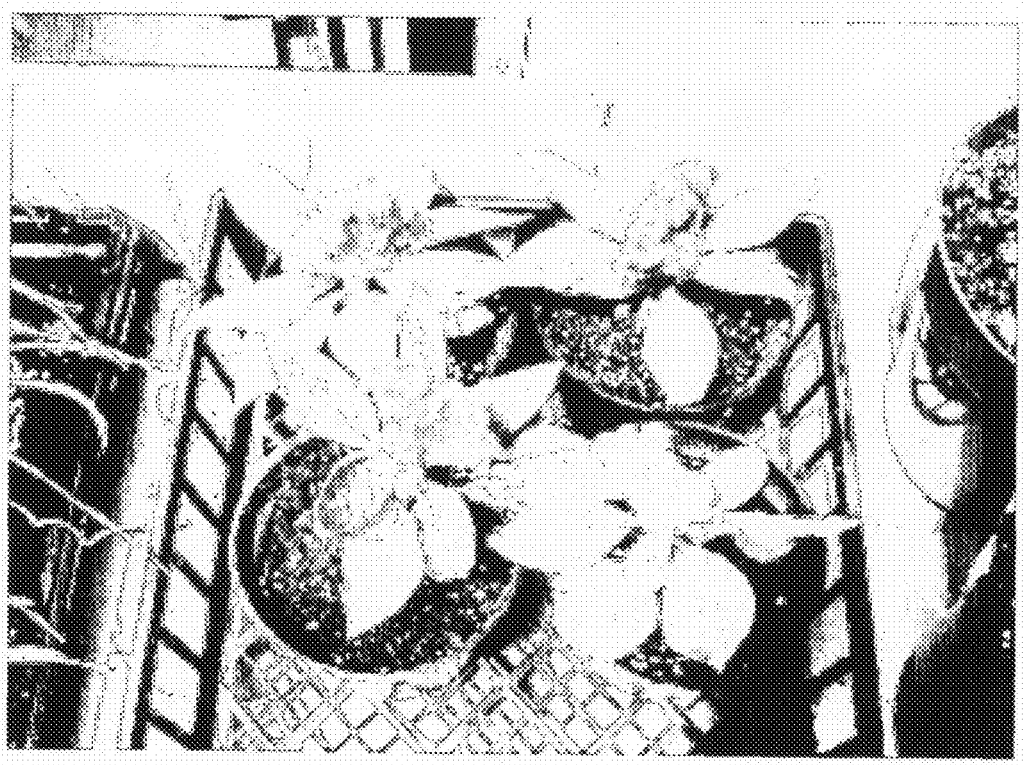
FIG. 4 shows *Celosia* 'cristata'. The cristata form of *Celosia* shows extensive fasciation which leads to production of an inflorescence that is flattened into a fan-like structure. PPFM bacteria isolated from these plants produce ten fold more cytokinin in culture than do PPFMs isolated from the 'plumosa' form of the plant.

*Celosia* is an ornamental plant with two distinct flower morphologies. One is called plumosa, the other cristata. See FIGS. 3 and 4. The fasciated stem and inflorescence of the cristata form are reminiscent of the phenotype of some plants after infection with a cytokinin-producing pathogen, so it was determined to isolate PPFMs from each of the two different flower types and to compare cytokinin production in them. Using the same methods described for the barley experiments described above, PPFM isolates from cristata inflorescences show 10 times higher cytokinin levels than those isolated from the plumosa form. Tying these observations into the earlier consideration of cytoplasmic male sterility, it is generally recognized that the plumosa form of the plant usually sets seed poorly (personal communication, Dr. David Brenner, curator of the Amaranthus collection, including *Celosia*, for the National Plant Germplasm System).

Example 7

Celosia seeds (cristata) were heated in order to lower PPFM populations. Some of these seeds were inoculated with PPFMs from cristata plants before planting; some were inoculated with PPFMs from plumosa plants. In parallel, unheated cristata seeds were inoculated either with plumosa or with cristata PPFMs. These plants have not yet flowered, but the alterations in the flowering phenotype should correlate with the origin of their PPFM inoculum. In a second related experiment, plumosa plants growing in the greenhouse have been treated with a foliar application of the cristata PPFMs.

Celosia is not the only ornamental plant in which its flower morphology may be altered with applications or inoculations of PPFM bacteria. Reynolds and Tampion (Reynolds, J & Tampion, J. 1983. *Double Flowers: A Scientific Study*. Scientific and Academic Editions, NY. 183 pp. ISBN 0-442-27844-6) document a number of instances in which cytokinins have been demonstrated to influence the development of a "double flowered" phenotype (an extreme case of male sterility). Thus, although the experiments described here were done on just few plant species, the results can reasonably be expected to apply to others, since cytokinins affect flowering in plants in general.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the following claims.

What is claimed is:

1. A method for increasing male fertility of a plant, comprising:
    (a) contacting seed of the plant with a Pink-Pigmented Facultative Methylotroph (PPFM) that in the aggregate produces a greater amount of cytokinin than a PPFM that was previously associated with the plant; and
    (b) planting the seed to produce a plant with increased male fertility.

2. The method according to claim 1, wherein said increasing fertility is indicated by increasing pollen count.

3. The method according to claim 1, wherein said plant is a dicot or a monocot.

4. The method according to claim 3, wherein said plant is soybean, barley, Arabidopsis, or Celosia.

5. The method according to claim 1, wherein said cytokinin is trans-Zeatin or its riboside or both.

6. The method according to claim 1, further comprising treating the seed to remove the previously associated PPFM before contacting the seed with the PPFM that produces a greater amount of cytokinin than the previously associated PPFM.

7. The method according to claim 1, comprising contacting the seed with more of the previously associated PPFM to produce more cytokinin in the aggregate.

8. A method for increasing male fertility of a plant comprising
    (a) contacting the plant with a PPFM that in aggregate produces a greater amount of cytokinin than a PPFM that was previously associated with the plant; and
    (b) testing the plant for its fertility by increasing pollen count.

9. The method according to claim 8, wherein the PPFM contacts the plant on its seed, its shoot or its root.

10. The method according to claim 8, wherein the plant is soybean.

11. The method according to claim 8, wherein the plant is barley.

12. The method according to claim 8, wherein the plant is Arabidopsis.

13. The method according to claim 8, wherein the cytokinin is trans-Zeatin or a riboside thereof or both.

14. The method according to claim 1, wherein the PPFM is a *Methylobacterium mesophilicum* which produces the greater amount of cytokinin.

15. The method according to claim 8, wherein the PPFM is *Methylobacterium mesophilicum* which produces the greater amount of cytokinin.

16. The method according to claim 8, wherein the PPFM is *Methylobacterium mesophilicum* which produces the greater amount of cytokinin.

17. The method of claim 1, wherein the plant is an ornamental variety plant.

18. The method of claim 8, wherein the plant is an ornamental variety plant.

* * * * *